(12) United States Patent
Peregrino Ferreira et al.

(10) Patent No.: US 6,323,006 B1
(45) Date of Patent: Nov. 27, 2001

(54) RECOMBINANT HUMAN BETA-CIS INTERFERON

(75) Inventors: Paulo Cesar Peregrino Ferreira; Erna Geessien Kroon; Romain Rolland Golgher; Claudio Antonio Bonjardim; Alex Fiorini De Carvalho, all of Belo Horizonte (BR)

(73) Assignee: Universidade Federal de Minas Gerais, Belo Horizonte (BR)

( * ) Notice: Subject to any disclaimer, the term of this patent is extended or adjusted under 35 U.S.C. 154(b) by 0 days.

(21) Appl. No.: 09/331,260

(22) PCT Filed: Dec. 19, 1997

(86) PCT No.: PCT/BR97/00082

§ 371 Date: Jul. 13, 1999

§ 102(e) Date: Jul. 13, 1999

(87) PCT Pub. No.: WO98/27211

PCT Pub. Date: Jun. 25, 1998

(30) Foreign Application Priority Data

Dec. 18, 1996 (BR) .................................................... 9606270

(51) Int. Cl.[7] ........................... C12N 15/22; C07K 14/565

(52) U.S. Cl. ..................................... 435/69.51; 536/23.52; 435/320.1; 530/351; 530/413; 424/85.6

(58) Field of Search ...................... 530/351, 413; 536/23.52; 435/320.1, 69.51; 424/85.6

(56) References Cited

U.S. PATENT DOCUMENTS

| | | | | |
|---|---|---|---|---|
| 4,588,585 | * | 5/1986 | Mark et al. | ........................... 530/351 |
| 5,166,322 | * | 11/1992 | Shaw et al. | ........................ 424/85.2 |
| 5,616,699 | | 4/1997 | Taniguchi et al. . | |

OTHER PUBLICATIONS

Carvalho et al., "Culture of Human Amniotic Cells: A System to Study Interferon Production", Nov. 1998. (Medline abst. of *Placenta* (England) 19(4):307–14, May 1998).

* cited by examiner

*Primary Examiner*—David L. Fitzgerald
(74) *Attorney, Agent, or Firm*—Young & Thompson

(57) ABSTRACT

The invention provides a new human interferon (IFN)-β variant cloned from an amniotic cell library, a cDNA encoding it, and processes for its production and purification. The variant, termed interferon beta-cis, differs from previously known hIFN-β isoforms by the substitution of a Cys residue for the Tyr present at position 60. Recombinant IFN beta-cis exhibits antiviral activity characteristic of IFN-β.

21 Claims, 5 Drawing Sheets

```
ATGAGCTACAACTTGCTTGGATTCCTACAAAGAAGCAGCAATTTTCAGTGTCAG
MetSerTyrAsnLeuLeuGlyPheLeuGlnArgSerSerAsnPheGlnCisGln

AAGCTCCTGTGGCAATTGAATGGGAGGCTTGAATACTGCCTCAAGGACAGGATG
LysLeuLeuTrpGlnLeuAsnGlyArgLeuGluTyrCisLeuLysAspArgMet

AACTTTGACATCCCTGAGGAGATTAAGCAGCTGCAGCAGTTCCAGAAGGAGGAC
AsnPheAspIleProGluGluIleLysGlnLeuGlnGlnPheGlnLysGluAsp

GCCGCATTGACCATCTGTGAGATGCTCCAGAACATCTTTGCTATTTTCAGACAA
AlaAlaLeuThrIleCisGluMetLeuGlnAsnIlePheAlaIlePheArgGln

GATTCATCTAGCACTGGCTGGAATGAGACTATTGTTGAGAACCTCCTGGCTAAT
AspSerSerSerThrGlyTrpAsnGluThrIleValGluAsnLeuLeuAlaAsn

GTCTATCATCAGATAAACCATCTGAAGACAGTCCTGGAAGAAAAACTGGAGAAA
ValTyrHisGlnIleAsnHisLeuLysThrValLeuGluGluLysLeuGluLys

GAAGATTTCACCAGGGGAAAACTCATGAGCAGTCTGCACCTGAAAAGATATTAT
GluAspPheThrArgGlyLysLeuMetSerSerLeuHisLeuLysArgTyrTyr

GGGAGGATTCTGCATTACCTGAAGGCCAAGGAGTACAGTCACTGTGCCTGGACC
GlyArgIleLeuHisTyrLeuLysAlaLysGluTyrSerHisCysAlaTrpThr

ATAGTCAGAGTGGAAATCCTAAGGAACTTTTACTTCATTAACAGACTTACAGGT
IleValArgValGluIleLeuArgAsnPheTyrPheIleAsnArgLeuThrGly

TACCTCCGAAACTGA
TyrLeuArgAsnEnd
```

Figure 2

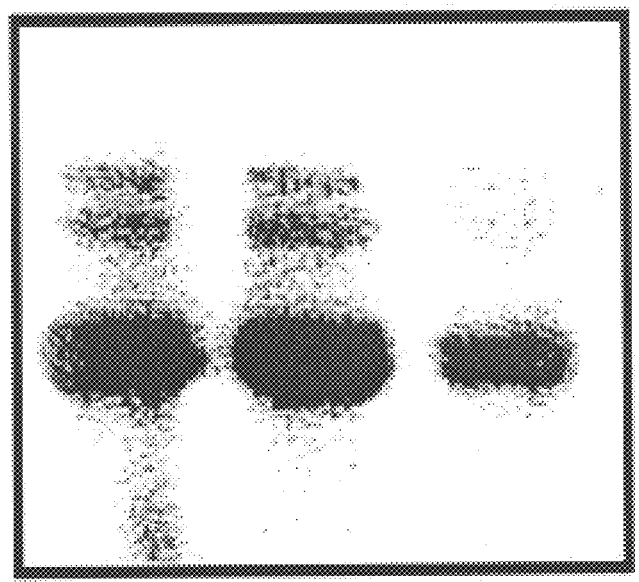
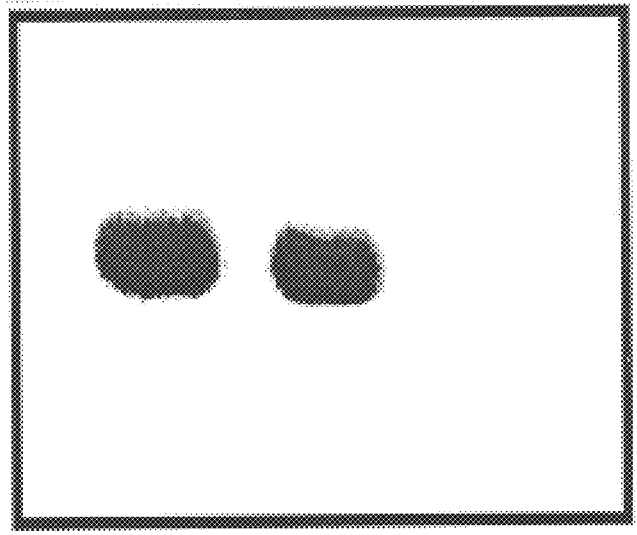
Figure 5

RECOMBINANT HUMAN BETA-CIS INTERFERON

TECHNICAL FIELD OF THE INVENTION

The present invention refers to the general field of the technology of recombinant proteins, for the production of the interferon beta-cis human mutant protein, to be used in human or veterinarian clinical applications or in research.

BACKGROUND OF THE INVENTION

Interferons (IFN) are a family of proteins whose first described biological activity was the ability to inhibit viral replication. Besides their antiviral action, IFNs possess a variety of other biological activities, controlling cell growth, differentiation, and modulating the immune system (Vilcek, J. & Sem, G. C. In *Virology* (Ed.) Fields, B. N., Knipe, D. M., Howley, P. M. 375–399, PA: Lippincott-Raven Publishers, 1996).

Human IFNs are classified in two major sub-families based on their biological and physical properties. The type I IFN family includes fibroblast β-interferon (IFN-β), leukocyte a-interferon (IFN-α) with 15 or more genes and pseudo-genes and IFN-ω and IFNτ. The type 11 IFN family is represented by IFN-γ, produced by T lymphocytes and NK cells in response to mitogens and antigenic stimuli (Vilcek, J. & Sem, G. C. In *Virology* (Ed.) Fields, B. N., Knipe, D. M., Howley, P. M. 375–399, PA: Lippincott-Raven Publishers, 1996).

Like in humans, most of the mammalian species have large IFN-α gene families. The existence of multiple IFN-β gene families was shown in bovine (three genes) whereas, humans and most of other mammalian species probably contain only one gene (Ryan, A. M., Gallagher, D. M., Womack, J. E *Mammalian Genome,* 3(19): 575–578,1992).

Placental tissues can produce IFNs. IFN activity has been detected in amniotic fluid, umbilical cord and blood of human placentae during pregnancy without clinical signs of viral infections (Lebon, P., Girard, S., Thepot, F. & Chany, C. *Journal of General Virology,* 59: 393–396, 1982) and also in mouse placental tissues (Fowler, A. K., Reed, C. D. & Giron, D. J. Nature, 285: 266–267, 1980). Ovine and bovine trophoblast cells produce another type of IFN named IFN-τ, during the embryo implantation into the uterus (Imakawa, K., Anthony, R. V., Kazemi, M., Mariotti, H., Poltes, H. G. & Roberts, R. M. *Nature,* 330: 377–379, 1987.). This IFN is necessary for fetal implantation, acting as an anti-luteolysin, resulting in the continued secretion of progesterone (Cross, J. C. & Roberts, R. M. *Proceedings of the National Academy of Sciences of the USA,* 88: 3817–3820, 1991). Recently a human trophoblast IFN (hTIFN) cDNA was described by (Whaley, A. E., Meka, C. S. R., Harbison, L. A., Hunt, J. S. & Imakawa, K *The Journal of Biological Chemistry,* 269:10864–10868, 1994) whose nucleotide sequence is similar (85%) to ovine and bovine IFN-τ. The HuIFNτ and HuIFN-ω mRNAs were detected in the cytotrophoblast cells throughout the pregnancy. This fact suggests that these IFNs are important as a first line of defence, protecting the fetus from virus transmission and also participating in the progressive changes of placental development (Whaley, A. E., Meka, C. S. R., Harbison, L. A., Hunt, J. S. & Imakawa, K *The Journal of Biological Chemistry,* 269:10864–10868, 1994). Human trophoblast cultures produced IFN-β, IFN-αI and tau interferon when infected by virus (Aboagye-Mathiesen, G., Thóth, F. D., Juhl, C. H., Norskov-Lauritsen, N. N., Petersen, P. M. & Ebbesen, P. *Journal of General Virology,* 71: 3061–3066, 1990 and Thóth, F. D., Norskov-Lauritsen, N. N., Juhl, C. H, Aboagye-Mathiesen, G. & Ebbesen, P. *Journal of General Virology,* 71: 3067–3069, 1990).

IFNs bind to receptors located at the cellular surface, activating in this way the transduction of cytoplasmic signals that will induce in the nucleus genes responsible for the activities of IFN (JOKLIK, W. K., Interferons, In: FIELDS, B. N. AND KNIPE, D. M. (Ed.) *Virology,* 2a. Ed.—New York, Raven Press Ltd., cap.16, p.383–410,1990).

All the members of the family of IFNs α possess a sequence of 165 to 166 a.a., of the which 4 cysteines (Cys) are highly conserved in the positions 1; 29; 98; 99 or 100; 138 or 139; and they are responsible for disulfide bonds (S—S). The S—S bonds between Cys 1; 98; 99 or 100 and between Cys 29 and 138 or 139 are important in the stabilization of the IFN structure (WETZEL, R. et al., *J. Interferon Rês.,* 1:381–389,1981). The bond among these two Cys is indispensable in the maintenance of the biological activity of this IFN (PATH, T., EMBO J., 11: 3193–3201 et al., 1992).

IFN β is produced by fibroblasts and it is a glycoprotein with relative molecular mass of 22–23 kDa and specific antiviral activity of 2–5×10$^8$ international units (protein Ul)/mg. A gene located at chromosome 9 codes this 166 a.a IFN that doesn't possess introns. IFN β of bovine, swine and caprine species are coded by multiple genes (OF MAEYER, E. M. and OF MAEYER-GUIGNARD, J.—*Interferon and other regulatory cytokines,* John Wiley and Sounds, New York, 1988).

IFN β possesses 3 cysteine residues (Cys) in the positions 17, 31 and 141. Two Cys 31 and 141 form a disulfide bond while Cys 17 stays free. The studies (MARK, D. F., et al., *Proc. Natl. Acad. Sci.* It USES, 81: 5662– 5666, 1984), in which the Cys 17 was changed for a serine showed that this IFN presented the same spectrum of biological activities of IFN β, such as anticellular and antiproliferative activity, activation of NK cells and neutralization of anti HuIFN antibodies, and presents a greater stability than natural HuIFN β when incubated at −70° C.

In other experiments, SHEPARD, H. M. et al., *Nature,* 294:563–565, 1981, changed the Cys 141 for a tyrosine, rendering a biologically inactive molecule.

The mechanisms through which IFNs induce the antiviral state have been delineated. It is accepted that the activation of the enzyme 2'5' oligoadenilate synthethase and of the RNA dependent protein kinase (dsRNA) are important in the antiviral action (PESTKA, S., et al., *Ann. Rev. Biochem.,* 56:727–777, 1987).

It is an object of the present invention to describe a new human protein, interferon beta-cis, isolated from primary cultures of human amniotic cells, the corresponding recombinant DNA molecule encoding it, and the process of production of the human recombinant protein interferon beta-cis produced through techniques of genetic engineering, to be used in human or veterinarian clinical applications or in research.

BRIEF DESCRIPTION OF THE DRAWINGS

These and other objects, features and many attendant advantages of the invention will be better understood upon a reading of the following detailed description when considered in connection with the accompanying drawings wherein:

FIG. 2: Nucleotide sequence and predicted translation of the interferon beta cis cDNA (SEQ ID NOS: 1 and 2).

FIGS. 5A–B: Induction of genes

DETAILED DESCRIPTION OF THE INVENTION

Figure 1:
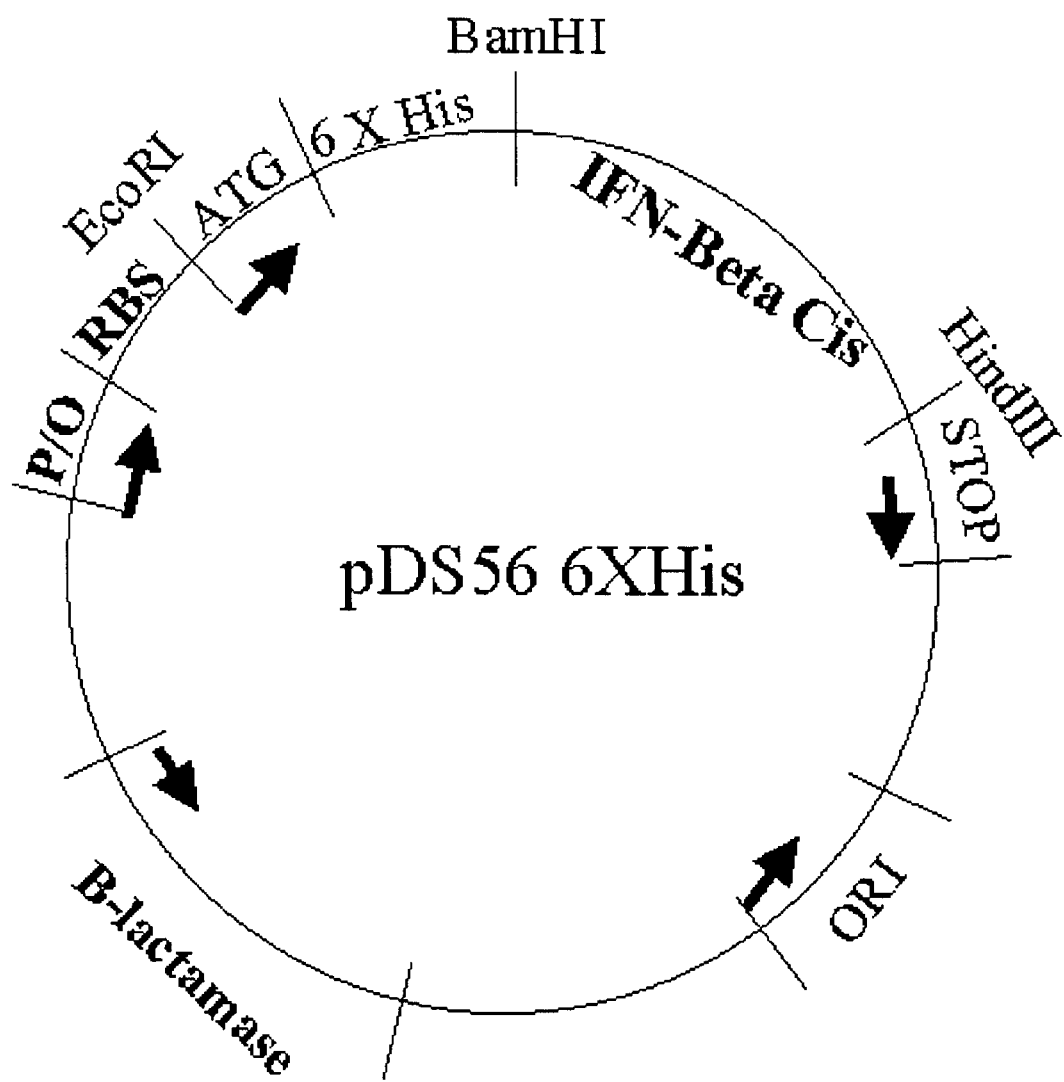
FIG. 1: The vector used for the expression of the interferon beta cis.
Figure 3:
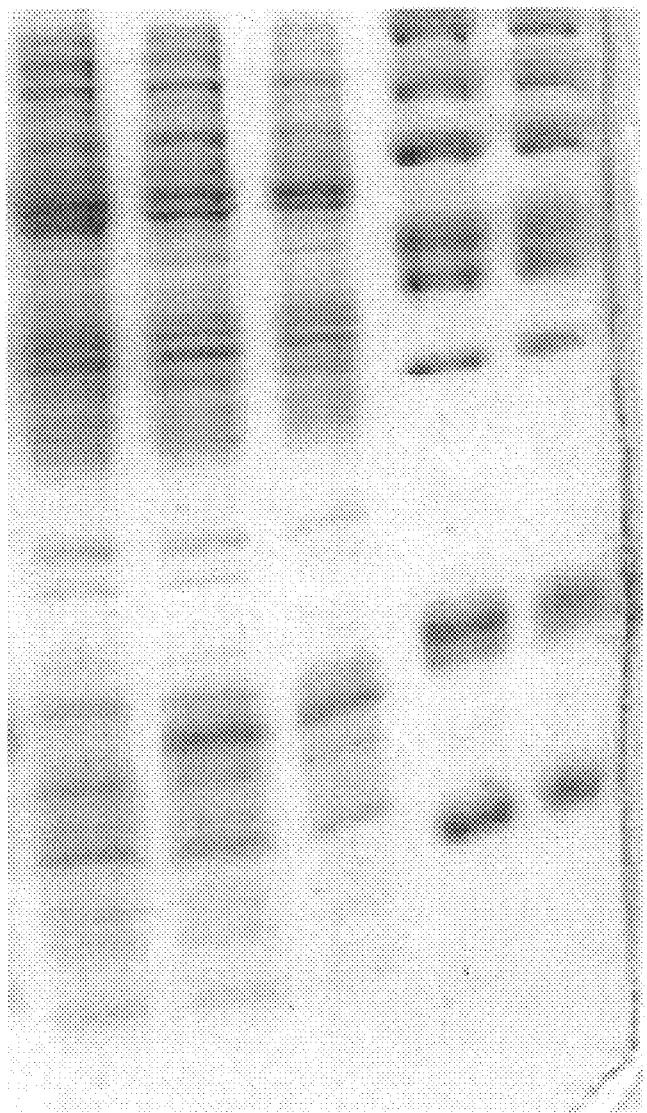
FIG. 3: Expression of beta cis interferon in *E. coli*.
Figure 4:
FIG. 4: Purification of beta cis interferon.

In order that this invention may be better understood the following examples, for illustrative purposes only, are described. The examples illustrate the present invention and are not intended to limit it in spirit or scope. The process can be understood better through the following description in consonance with the examples.

EXAMPLE 1
Primary Culture of the Human Amniotic Cells (1)

Primary culture of the human amniotic cells was established by using amniotic membranes that were separated from the placenta, washed in a saline solution and cut in fragments of approximately 1 $cm^2$. The fragments were digested with trypsin (0.25–0.30%) in the proportion of 5 to 7 ml per gram of tissue. After each stage of treatment with trypsin the cells were centrifuged and cultured in minimum essential medium containing Eagle's salts at a density of 15 to $25 \times 10^6$ cells per Petri dish.

EXAMPLE 2
Induction of Interferon (2)

One week after implantation the cells were infected with Sendai virus or Newcastle Disease Virus in the proportion of 3.0 to $4.8 \times 10^{-6}$ haemagglutinating units of virus per cell for 1 hour and were again incubated for 4 to 8 hours.

EXAMPLE 3
RNA Extraction and Purification (3,4,5,6,7,8)

For RNA extraction the infected cells were washed with saline. and disrupted with 3.5 to 4.5 ml of a 3 to 4 M guanidine isothiocyanate solution on ice for 10 to 20 min. For the purification of the RNA 1.5 to 2.0 ml of a solution of cesium chloride (5.7 to 5.8 M) were added, and centrifuged at 114.000 g during 18 to 24 hours at 20°–24° C. RNA was homogenized in a Tris-EDTA solution and the extraction was made with the same volume of phenol/chloroform/isoamyl alcohol in the proportion 25:24:1, shaken in a vortex mixer, and centrifuged. RNA was precipitated with 1/10 of the volume of sodium acetate (2 to 3 M, pH 5.5 to 6.0) and ethanol, centrifuged and the pellet was dissolved in water.

EXAMPLE 4
cDNA Synthesis (9,10)

5 to 10 µg of RNA was used as template for the synthesis of the first cDNA strand using, 0.5 to 1 µg of primer T15, pyrophosphate 40–50 mM, 20 to 30 U of avian reverse transcriptase and its buffer.

The amplification of the fragment corresponding to the interferon starting from the cDNA obtained in the steps 1, 2, 3, 4, 5 6,7,8,9 or starting from the vector that contains the cloned DNA of the interferon beta-cis gene was carried out using specific oligonucleotides (5'GCCGGATCCTACMCTTGCTT GGATTCCTA3 (SEQ ID NO: 3) and 5'GCCMGCTTAGTTTCGGTCATTCCTGTMGTC3') (SEQ ID NO: 4) for the region of the corresponding fragment of the protein (interferon β) that contains the sites for the restriction enzymes BamH 1 and Hind III, in the polymerase chain reaction (PCR).

The reaction was made with Taq polymerase buffer (500 mM KCl, 100 mM Tris-HCl pH 9.0–9.5, 1.5–2.5 mM $MgCl_2$ and 1–2% triton X-100), 0.1–1 U of Taq polymerase (Promega, USA, Cat. no. M186A), 0.5–1.5 mM $MgCl_2$, 20–50 mM of each nucleotide (dATP,dCTP,dGTP,dTTP) 10–30 pmoles of each primer, and 0.01a 0.1 ng cDNA and distilled and sterile water, q.s.p. 50–100 µl. The reaction was run for 1–2 cycles at 94–96° C.1–2 min; 53 to 55° C./1–2 min.; 70–72° C./1–2 min; 30 cycles at 94–96° C./1 to 2 min; 36–38° C./1–2min; 70–72° C./1–2 min and more 1 cycle to 94–96° C./1–2 min; 36–38° C./1 to 2 min; 70–72° C./10–15 min.

EXAMPLE 5
Fractionation and Purification of DNA (11,12)

The fractionation of the DNA was accomplished in agarose gel (1.5–2.0%). The purification of the amplified DNA was made by cutting out the band of the gel. The band was diluted in 2–3 the volumes of NaI solution (NaI 8M+0.022 M DTT) and sodium phosphate buffer (1M pH 6.0–6.5) and incubated for 5–10 min. at 50–56° C. Glass spheres were added to the suspension, mixed, incubated 1–5 min. at room temperature and centrifuged 10–30 seconds. The spheres were washed with Ethanol buffer (75% of Ethanol, 0.01 M Tris-HCl, pH 7.0–7.6, 0.01 M EDTA, pH 8.0–8.5). The DNA was eluted from the glass spheres with buffer (Tris pH 7.0–7.4 10 mM, 1–3 mM EDTA) at 50–56° C. for 1–5 min.

EXAMPLE 6
Digestion of DNA Fragment and Cloning (13,14)

For the digestion of the DNA, the product was first treated with enzyme Hind III in a reaction with 10–20 U of Hind III (Biolabs, England), 3–5 µl buffer I (Promega, USA) and distilled water qsp 30–50 µl, with incubation at 37° C. for 2–4 h. After that, 10–20 U of Bam HI (Biolabs, England), 5–10 µl of REACT III (BRL, USA), $H_2O$ (dd) qsp 50–100µl was added to the tube and incubated at 37° C. for 2–4 h. For cloning of the DNA fragment in the plasmid PDS-56 (FIG. 1), the digestion of the vector was accomplished with the restriction enzymes Hind III and Bam HI in a reaction containing the vector, 10–20 U of enzyme Hind III (Promega, USA), 2–5 µl buffer (Promega, USA), and distilled water qsp 20–50 µl, with incubation at 37° C. for 2–4 h. Later 10–20 U of the enzyme Bam HI (Promega, USA), 5–10 µl of react III (BRL, E.U.A), and distilled water qsp 50–100 µl were added to the reaction and incubated at 37° C. for 24 h. The product of this digestion was analyzed in a 1% agarose-TAE gel electrophoresis. The band corresponding to the digested plasmid was cut out of the gel and transferred to an eppendorf tube (1.5 ml) and purified.

EXAMPLE 7
Ligation, Transformation and Clone Selection (15,16,17)

In the ligation reaction of the DNA fragment 20–50 ng of the insert was added to 5–15 ng of the vector, 0.5–2.0 U of T4 ligase (Promega, USA), ATP 5 mM (Promega, USA), ligation buffer (Promega, USA), $H_2O$ (dd) qsp 15 µl, with incubation at 14–16° C. (BOD, FANEN, Brazil) for 12–18 h.

The bacterial transformation was done with *Escherichia coli* bacteria. The volume of the ligation reaction was made up to 40–60 µl with buffer (Tris 10 mM pH 7.2–7.4, EDTA 1 mM) and of 100 µl of a suspension of competent bacteria were added. The tubes were slightly rotated and immediately incubated in ice bath for 20–40 min., submitted to a thermal shock at 40–42° C. for 1–3 min. and again in ice bath for 20–40 seconds. LB Medium (Bacto triptone 1% p/v, yeast extract 0.5% p/v, NaCl 171 mM) without antibiotics was added at double the volume and incubated for 37° C. by 1–2 h. The bacteria were centrifuged, homogenized in LB and inoculated in Petri plates with LB agar (agar 1.5% p/v, yeast extract 0.5% p/v, triptone 0.1% p/v, NaCl 0.5% p/v pH 7.2–7.5) with 50–200 µg/ml ampicillin and 20–100 µg/ml Kanamicin. The plates were incubated at 37° C. for 15–24 h. For the selection of the positive clones they were grown in LB with 50–200 μg/ml ampicillin and 20–100 μg/ml Kanamicin at 37° C. under agitation for 15–20 h. After incubation PCR using specific primers of the vector (for amplification of the region corresponding to the insert) being the primer (sense) 5'-TTCATTAAAGAGGAGAAATT-3' (SEQ ID NO: 5) and primer (anti-sense) 5'-CTATCMCAGGAGTCCMGC-3'(SEQ ID NO: 6). The reaction was made with Taq. polymerase 10×buffer (KCl 500 mM, Tris-HCl 100 mM pH 9.0–9.5, MgCl$_2$ 15–25 mM and triton X-100 1–2%), 0.5–1.0 U of Taq polymerase (Promega, USA), 0.5–1.5 mM MgCl$_2$ 20–50 mM of each nucleotide (dATP, dCTP, dGTP, dTTP), 10–30 pmoles of each primer, 0.5–1 μl of bacterial suspension and sterile dd water qsp 20–40 μ. The reaction was processed with 1–3 cycles for 94–96° C./5min., 50–55° C./1–2 min., 70–72° C./1–2 min.; 30 cycles at 94–96° C./30–45 sec., 45–50° C./30–45 sec., 70–72° C./30–45 sec. and 1 cycle at 94–96° C./1–2 min., 45–50° C./1–2 min., 70–72° C./10–15 min. The product of this reaction was electrophoresed in agarose gel at 1–2%.

EXAMPLE 8
Sequencing (18)

The positive clones were sequenced to identify the mutant interferon beta-cis (FIG. 2).

EXAMPLE 9
Protein Production, Induction and Lysis of Bacteria (19,20, 21)

The positive clones for the mutant interferon beta-cis were used for the production of the protein and they were grown in LB medium with 50–200 μg/ml ampicillin and 50–200 μg/ml of Kanamicin and incubated at 37° C. under agitation until the optical density (OD 600 nm) of 0.5–0.7. Then for the induction of the protein (20), 0.2–0.4 M IPTG (Isopropyl-(-D-thiogalacoside) was added and incubated for 3–5 h. The bacteria (21) were centrifuged, the supernatant discarded and the pellet homogenized in buffer A(Guanidine-HCl 5–6 M, sodium phosphate 0.1–0.2 M, Tris 0.01–0.02 M pH 7.8–8.0) with agitation for 1–2 h.

EXAMPLE 10
Protein Purification (22)

The supernatant was applied to a column with Ni-NTA resin. For the purification of the protein the column was washed sequentially with buffer A, buffer B (Urea 7–8 M, phosphate of sodium 0.1–0.2 M, Tris 0.01–0.02 M pH 7.8–8.0) and with buffer C (Urea 7–8 M, phosphate of sodium 0.1–0.2 M, Tris 0.01–0.02 M pH 7.0–7.2). The protein was eluted with buffer D (Urea 7–8 M, sodium phosphate 0.1–0.2 M, Tris 0.01–0.02 M pH 5.0–5.2) and sequentially with (Urea 7–8 M, phosphate of sodium 0.1–0.2 M, Tris 0.01–0.02 M pH 4.0–4.2); fractions and a sample of 50 μl were collected and each fraction was diluted v/v in sample buffer, heated for 10 min. and submitted to electrophoresis in polyacrilamide gel (SDS-PAGE). The gel was analyzed for the presence of the fraction that contained the corresponding band to the protein interferon beta-cis protein.

While the present invention has been described in connection with examples, it will be understood that modifications and variations apparent to those ordinary skill in the art are within the scope of the present invention.

What is claimed is:

1. A recombinantly produced interferon-β-cis polypeptide comprising the amino acid sequence shown in SEQ ID NO: 2.

2. A polypeptide according to claim 1 consisting of the amino acid sequence shown in SEQ ID NO: 2.

3. An isolated nucleic acid molecule encoding an interferon-β-cis polypeptide according to claim 1.

4. A nucleic acid molecule according to claim 3 comprising the nucleotide sequence shown in SEQ ID NO: 1.

5. A vector comprising the sequence of a nucleic acid molecule according to claim 3.

6. A vector according to claim 5 comprising the nucleotide sequence shown in SEQ ID NO: 1.

7. A process for preparing an interferon-β-cis polypeptide comprising introducing a nucleic acid according to claim 3 into a host cell and culturing the cell under conditions suitable to effect expression of the nucleic acid and production of the polypeptide.

8. A process according to claim 7 wherein the host cell is a bacterium.

9. A process according to claim 8 wherein the bacterium is *E. coli*.

10. A process according to claim 7 further comprising recovering the polypeptide from the cultured cell.

11. A process according to claim 10 wherein the polypeptide is recovered by nickel chelate affinity chromatography.

12. A recombinantly produced human interferon-β polypeptide wherein the amino acid residue $Tyr^{60}$ is replaced by $Cys^{60}$.

13. An isolated nucleic acid molecule encoding a polypeptide according to claim 12.

14. A nucleic acid molecule according to claim 13 wherein the nucleic acid molecule is a cDNA molecule prepared from a human amniotic cell library.

15. A cDNA molecule according to claim 14 prepared by a process comprising amplifying DNA from the library with primers having the sequences shown in SEQ ID NOs: 3 and 4.

16. A vector comprising the sequence of a nucleic acid molecule according to claim 14.

17. A process for preparing a $Cys^{60}$-substituted interferon-β polypeptide comprising introducing a nucleic acid according to claim 14 into a host cell and culturing the cell under conditions suitable to effect expression of the nucleic acid and production of the polypeptide.

18. A process according to claim 17 wherein the host cell is a bacterium.

19. A process according to claim 18 wherein the bacterium is *E. coli*.

20. A process according to claim 17 further comprising recovering the polypeptide from the cultured cell.

21. A process according to claim 20 wherein the polypeptide is recovered by nickel chelate affinity chromatography.

* * * * *

SEQUENCE LISTING

<160> NUMBER OF SEQ ID NOS: 6

<210> SEQ ID NO 1
<211> LENGTH: 501
<212> TYPE: DNA
<213> ORGANISM: Homo sapiens
<220> FEATURE:
<221> NAME/KEY: CDS
<222> LOCATION: (1)..(498)

<400> SEQUENCE: 1

```
atg agc tac aac ttg ctt gga ttc cta caa aga agc agc aat ttt cag        48
Met Ser Tyr Asn Leu Leu Gly Phe Leu Gln Arg Ser Ser Asn Phe Gln
  1               5                  10                  15 tgt cag aag ctc ctg tgg caa ttg aat ggg agg ctt gaa tac tgc ctc        96
Cys Gln Lys Leu Leu Trp Gln Leu Asn Gly Arg Leu Glu Tyr Cys Leu
             20                  25                  30 aag gac agg atg aac ttt gac atc cct gag gag att aag cag ctg cag       144
Lys Asp Arg Met Asn Phe Asp Ile Pro Glu Glu Ile Lys Gln Leu Gln
         35                  40                  45 cag ttc cag aag gag gac gcc gca ttg acc atc tgt gag atg ctc cag       192
Gln Phe Gln Lys Glu Asp Ala Ala Leu Thr Ile Cys Glu Met Leu Gln
     50                  55                  60 aac atc ttt gct att ttc aga caa gat tca tct agc act ggc tgg aat       240
Asn Ile Phe Ala Ile Phe Arg Gln Asp Ser Ser Ser Thr Gly Trp Asn
 65                  70                  75                  80 gag act att gtt gag aac ctc ctg gct aat gtc tat cat cag ata aac       288
Glu Thr Ile Val Glu Asn Leu Leu Ala Asn Val Tyr His Gln Ile Asn
                 85                  90                  95
```

-continued

```
cat ctg aag aca gtc ctg gaa gaa aaa ctg gag aaa gaa gat ttc acc      336
His Leu Lys Thr Val Leu Glu Glu Lys Leu Glu Lys Glu Asp Phe Thr
            100                 105                 110 agg gga aaa ctc atg agc agt ctg cac ctg aaa aga tat tat ggg agg      384
Arg Gly Lys Leu Met Ser Ser Leu His Leu Lys Arg Tyr Tyr Gly Arg
        115                 120                 125 att ctg cat tac ctg aag gcc aag gag tac agt cac tgt gcc tgg acc      432
Ile Leu His Tyr Leu Lys Ala Lys Glu Tyr Ser His Cys Ala Trp Thr
    130                 135                 140 ata gtc aga gtg gaa atc cta agg aac ttt tac ttc att aac aga ctt      480
Ile Val Arg Val Glu Ile Leu Arg Asn Phe Tyr Phe Ile Asn Arg Leu
145                 150                 155                 160 aca ggt tac ctc cga aac tga                                          501
Thr Gly Tyr Leu Arg Asn
                165
```

<210> SEQ ID NO 2
<211> LENGTH: 166
<212> TYPE: PRT
<213> ORGANISM: Homo sapiens

<400> SEQUENCE: 2

```
Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Cys Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:Synthetic

<400> SEQUENCE: 3
gccggatcct acaacttgct tggattccta                                      30

<210> SEQ ID NO 4
<211> LENGTH: 32
<212> TYPE: DNA
<213> ORGANISM: Artificial Sequence -continued

```
<220> FEATURE:
<223> OTHER INFORMATION: Description of Artificial Sequence:Synthetic

<400> SEQUENCE: 4
gccaagctta gtttcggtca ttcctgtaag tc                                32

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 5
ttcattaaag aggagaaatt                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 6
ctatcaacag gagtccaagc                                              20
```